United States Patent
Razavi et al.

(10) Patent No.: US 8,527,069 B2
(45) Date of Patent: Sep. 3, 2013

(54) STERNAL CLOSURE WIRE FOR SENSING AND THERAPEUTIC ENERGY DELIVERY

(75) Inventors: Mehdi Razavi, Houston, TX (US); Alan Brewer, Houston, TX (US)

(73) Assignee: Texas Heart Institute, Houston, TX (US)

( * ) Notice: Subject to any disclaimer, the term of this patent is extended or adjusted under 35 U.S.C. 154(b) by 143 days.

(21) Appl. No.: 13/104,534

(22) Filed: May 10, 2011

(65) Prior Publication Data

US 2011/0282162 A1 Nov. 17, 2011

Related U.S. Application Data

(60) Provisional application No. 61/333,604, filed on May 11, 2010.

(51) Int. Cl.
*A61N 1/00* (2006.01)
*A61B 5/04* (2006.01)

(52) U.S. Cl.
USPC ........... 607/126; 600/372; 600/509; 607/119; 607/132

(58) Field of Classification Search
USPC .................. 600/301, 325, 361, 372–375, 377, 600/381, 508–509, 549; 607/115–116, 126
See application file for complete search history.

(56) References Cited

U.S. PATENT DOCUMENTS

| | | | |
|---|---|---|---|
| 5,217,027 A * | 6/1993 | Hermens | 607/126 |
| 5,350,419 A * | 9/1994 | Bendel et al. | 607/132 |
| 5,423,876 A * | 6/1995 | Camps et al. | 607/116 |
| 5,738,105 A * | 4/1998 | Kroll | 600/510 |
| 5,792,217 A * | 8/1998 | Camps et al. | 607/119 |
| 2003/0125787 A1* | 7/2003 | Shchervinsky | 607/132 |
| 2008/0262378 A1* | 10/2008 | Gerber et al. | 600/549 |

OTHER PUBLICATIONS

Yasir Abu-Omar, et al., "Indications and positioning of temporary pacing wires," May 12, 2006, pp. 1-10.

* cited by examiner

*Primary Examiner* — Linda Dvorak
*Assistant Examiner* — Brian M Antiskay
(74) *Attorney, Agent, or Firm* — Trop, Pruner & Hu, P.C.

(57) ABSTRACT

An embodiment includes a sensor coupled to a sternal closure wire. The sternal closure wire holds two sternum portions of a patient adjacent to one another and the first sensor senses a biological signal of the patient. An embodiment includes a current source coupled to a sternal closure wire. The sternal closure wire holds two sternum portions of a patient adjacent to one another, and the current source delivers an electrical current to the patient via the sternal closure wire. Other embodiments are described herein.

16 Claims, 4 Drawing Sheets

FIG. 4
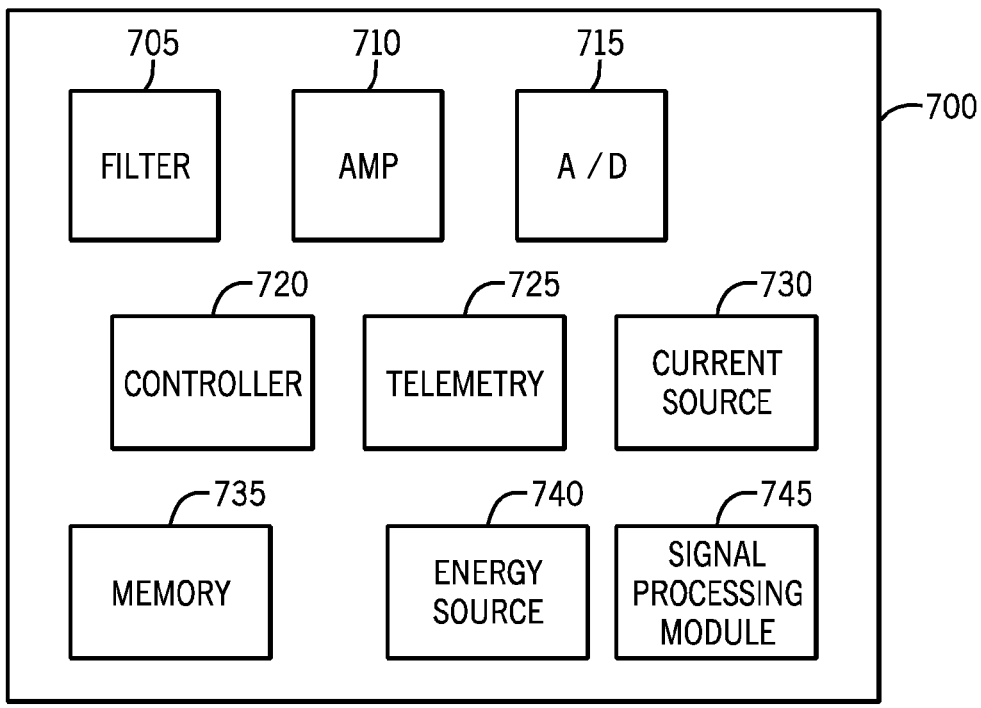
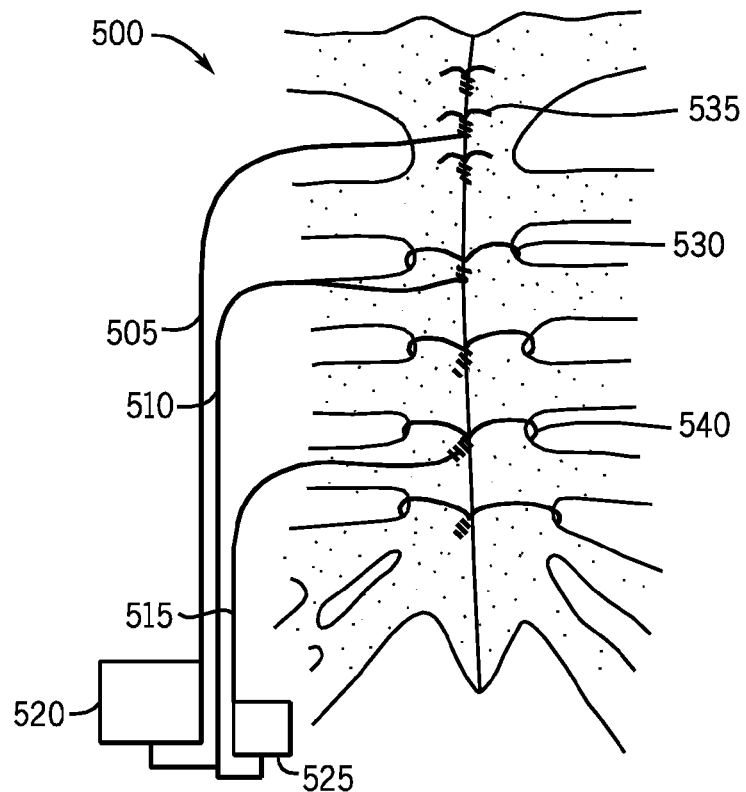
FIG. 5

STERNAL CLOSURE WIRE FOR SENSING AND THERAPEUTIC ENERGY DELIVERY

This application claims priority to U.S. Provisional Patent Application No. 61/333,604 filed on May 11, 2010 and entitled "METHODS, DEVICES, AND SYSTEMS OF COMBINING STERNAL CLOSURE WITH IMPLANTABLE SENSORS AND THERAPEUTIC DEVICES", the content of which is hereby incorporated by reference.

BACKGROUND

Thoracic surgery frequently involves the surgical creation of a mid-line sternotomy, which is an opening of the chest by some method of cutting through the skin, muscle, cartilage and bone of the central chest and spreading this surgical opening. Commonly this is done to allow additional surgery within the thoracic cavity. Examples of these surgeries include, but are not limited to, coronary artery bypass graft surgery (CABG) and heart valve replacement surgery. Such surgeries may require the patient be supported with cardio-pulmonary bypass. Thoracic surgeries may employ other surgical access techniques besides the mid-line sternotomy. When the surgical opening is closed, sternal wires may be used to do so.

Sternal wires or high-tensile-strength suture material may be employed to affect the closing of a surgical access site due to their high tensile-strength and ability to remain closed or tied. The high strength of such wires helps the surgeon properly approximate the alignment of the tissues (including bone and cartilage) on either side of the sternotomy and maintain this alignment while the sternum heals. Sternal wires may be used with other surgical access sites. For example, such wires may be used in orthopedics to couple or connect other tissues such as bone.

Because many thoracic surgeries are extremely invasive patients often require a significant degree of post-operative monitoring. Such monitoring might include, but is not limited to, monitoring of the patient's electrocardiogram (ECG), body temperature, blood oxygen saturation level, local sounds, and/or electrical impedance between two or more locations. This helps a medical staff minimize the impact to the patient of complications from the surgery should these develop, as well as to generally expedite the patient's recovery from surgery. Such monitoring may continue for an indefinite period of time, including long-term outpatient care. Unfortunately, monitoring modalities external to the patient may be unwillingly disconnected from the patient. Such monitoring is also subject to interference from nearby devices and may have some degree of inaccuracy for values considering the distance from the source.

Also, because thoracic surgeries are extremely invasive, patients may require therapeutic interventions during convalescence such as, for example, temporary cardiac pacing, cardiac defibrillation, and synchronous cardio-version of abnormal cardiac rhythms. Such therapeutic interventions may be emergently needed and potential life-saving (e.g., cardiac defibrillation for ventricular fibrillation). Therapeutic intervention devices external to the patient may be vulnerable to unintended functional disconnection from the patient, may cause pain when current transmits through due to the patient's skin, may be susceptible to mechanical damage, liquid intrusion, and the like, may be more susceptible to infection compared to fully-implantable systems, and may be less energy-efficient and effective than implantable counterparts because the therapeutic current is partially dissipated when passing through the patient's skin and other tissues.

BRIEF DESCRIPTION OF THE DRAWINGS

Features and advantages of the present invention will become apparent from the appended claims, the following detailed description of one or more example embodiments, and the corresponding figures, in which:

FIG. 4 includes a block schematic for a system in an embodiment of the invention.

FIG. 5 includes a schematic of a system in an embodiment of the invention.

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

As used herein, "wire" includes metallic, non-metallic, and/or hybrid metallic/non-metallic suture and systems that grab, pull, push, and/or hold tissues on either side of an incision or wound in a desired alignment. "Sternal wire", "chest wire", and the like include systems used to approximate alignment of tissues (e.g., bone and cartilage) on either side of a thoracic incision or wound and maintain the alignment while the incision or wound heals. "Chest closure", "sternal closure", and the like mean the closure of a sternotomy or other thoracotomy incision/wound.

Figure 1:
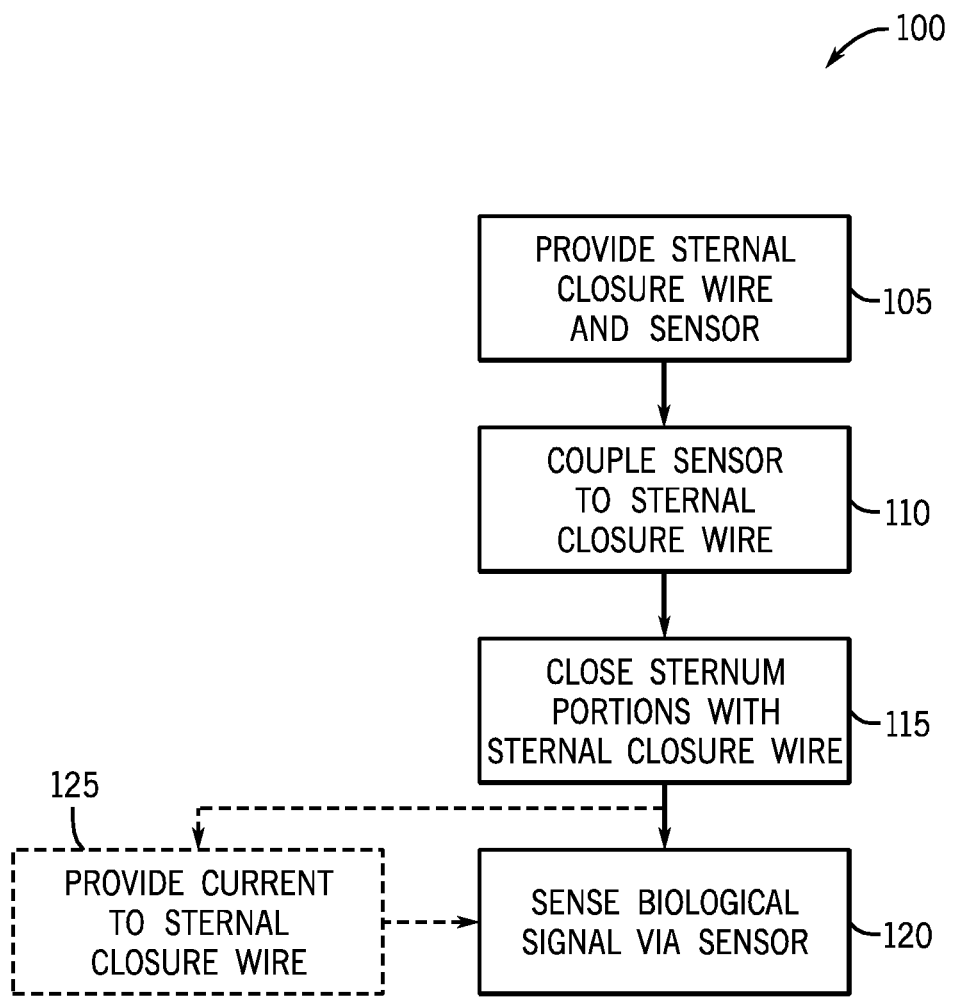
FIG. 1 includes a schematic flow chart in an embodiment.
Figure 2:
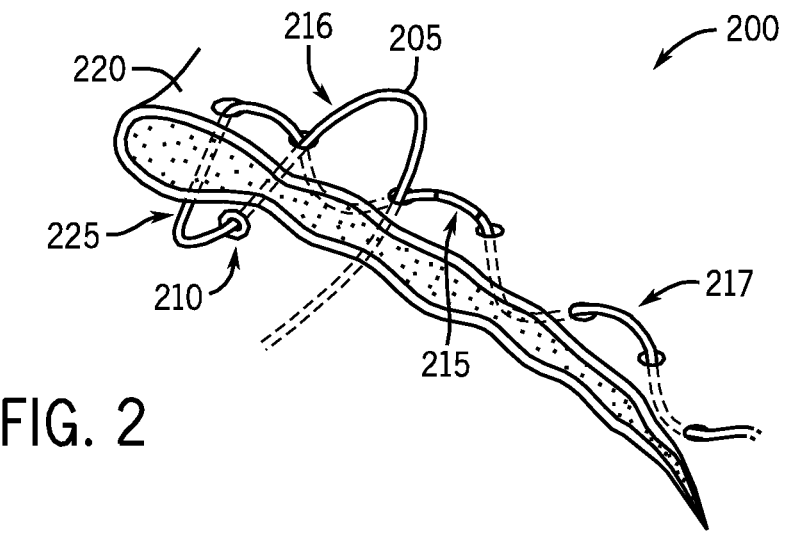
FIG. 2 includes a schematic of a system in an embodiment of the invention.

FIG. 1 includes a schematic flow chart for a method 100 in an embodiment. Block 105 includes providing a sternal closure wire and a first sensor. Block 110 includes coupling the first sensor to the sternal closure wire. For example, FIG. 2 includes a system 200 in an embodiment where sternal closure wire 205 is coupled to sensor 210. FIGS. 1 and 2 are addressed below.

Sensor 210 may be toroidal or donut shaped. The inner ring of sensor 210 may include an exposed conductive surface to interface (i.e., electrically communicate or couple) a conductive surface of wire 205. Block 115 includes coupling two sternum portions of a patient to one another via sternal closure wire 205. To promote clarity, only one such sternum portion 220 is shown in FIG. 2. Block 120 includes sensing a biological signal of the patient via sensor 210. The biological signal may include, without limitation, ECG, cardiac output, stroke volume, temperature, pH, oxygen saturation, heart rate, and respiration.

Sensor 210 may include more than circuitry strictly related to pure sensing. For example, sensor 210 may include a processor(s) or controller (s), filters (e.g., analog, digital, or mixed signal processing filters), A/D converters, amplifiers, antennae, power source, and the like used to collect a signal, process the signal (to varying degrees depending on the embodiment), and communicate the signal (e.g., to an external interrogation unit). Accordingly, sensor 210 may include modules to processes the first biological signal to generate a processed signal, and transmit the processed signal to the user. Wire 205 is shown as a wire suture, however, wire 205 may also include staples and other closure devices. "Wire" includes staples and closure systems (e.g., systems formed from band or wire-like lengths of material), which are included in embodiments of the invention.

In an embodiment, wire 205 includes insulated portions. For example, wire 205 may include a first portion 216 covered by a first outer insulation covering, a second portion 217 covered by a second insulation covering, and a portion 215 that is not covered by an insulation covering. For example, the user (e.g., physician, surgeon, surgical assistant) may not know exactly where a certain potion of wire will be upon final adjusting and closing of the tissues. However, after (or nearly after) determining the final location for the wire the user may elect to remove one or more portions of insulation to selectively expose (i.e., conductively) certain portions of the wire (e.g., 215) to the patient. Thus, user can selectively remove insulation coverings to vary exposure of an electrical conductive surface of the sternal closure wire to the patient. Removable portions of insulation may include perforations that aid the surgeon in removing the insulation in a desired location. Removal may occur before the wire is introduced into the body, during suturing by the surgeon, and/or after the wire has been secured in its final position. Other embodiments may not include insulation areas that can be removed but instead may offer sternal wire that arrives to the user with one or more areas uncovered by insulation with other areas covered. Still other embodiments include little to no insulative covering on the wire.

In an embodiment, a system may include a first electrode that includes the sternal closure wire. For example, in FIG. 2 wire 205 may be used as an electrode to sense ECG signals. If wire 205 includes little if any insulation covering then large portions of wire 205 may be used as an electrode to gather in ECG data and transmit that ECG data or signal to sensor 210. However, the user may wish to limit the electrode and thus, via use of insulative covering, only expose a certain region of wire (e.g., area 215). As a result, the uncovered portion may provide an electrode surface at a specific location. For example, the electrode surface may be on an internal portion (e.g., near portion 225) that is close to the heart but shielded somewhat from noise external to rib cage. Also, insulation may be removed only at more distal location(s) of wire 205 to generate a desired lead (e.g., LA, RA, LL, V1, V2, V3, V4, V5, V6) and signal (e.g., I, II, III, aVR, aVL, aVF, V1, V2, V3, V4, V5, V6). Such leads may also be used to calculate heart rate (HR) and the like. In another embodiment section 215 may instead be an area covered by insulation while other areas 216, 217 are not covered by insulation.

In an embodiment, a sternal closure wire includes a first portion having a first electrical conductivity and a second portion having a second electrical conductivity unequal to the first electrical conductivity. Consequently, a current source may deliver more current to a patient via the first portion than with the second portion. For example, a sternal wire need not be monolithic but instead may be formed of various segments, some of which include different materials with different electrical conductivities. Some segments may be metals (strong conductors) and other segments may be more insulating (poor conductors). Thus, the metal sections may serve as electrodes or otherwise as conduits for current (sensing and/or therapeutic). In other embodiments, the areas of unequal electrical conductivity may be due to some areas having insulative covering and other areas including no such covering. Many materials may be used to produce a sternal wire electrode. For example, metal systems with high strength and resistance to degradation from body fluid exposure include stainless steel (e.g., SS316) and medical implantable alloys such as F562/MP35N Cobalt-Chromium-Molybdenum, Titanium Ti-6AL-4V, F75/Stellite 21 Cobalt-Chromium-Molybdenum (CoCroMO), F90/Stellite 25 Cobalt-Chromium-Molybdenum and Nitinol. If different segments are present, they may be fused to one another (e.g., welding, knotted together, and the like).

Again regarding FIG. 2, toroid sensor 210 may slidably couple to wire 205 so a user may determine a final installation location 225 for the first sensor (e.g., along sternal closure wire 210) from a plurality of final installation locations (e.g., 225, 216, 215, 217) and slidably couple the first sensor to the sternal closure wire at the final installation location. As a result, the slidable sensor provides the user with a plurality of final installation locations for the first sensor 210 along the sternal closure wire 205.

In an embodiment, sensors (e.g., bead sensors like sensor 210) may be secured to a wire (or any other method of chest closure or sternal closure) by various methods not limited to the sternal wire passing through a hole in the bead. For example, a bead sensor may include a grooved and crimpable region. The user aligns the groove over a desired location along the length of a sternal wire and uses a crimping tool to compress the grooved region such that it grips the wire and securely retains (i.e., affixes) the bead to the wire. Beads may also be secured by threaded retention systems, various clips which may be either separate from or integrated with the bead, glues, adhesives, and combinations thereof.

Method 100 may optionally include some or all of the blocks depicted in FIG. 1. One optional block is block 125. Sensor 210 may include (or be coupled to) a current source. The current source may couple to sternal closure wire 205 so the user can deliver an electrical current to sternal closure wire 205. Then, in block 120 the user can sense the first biological signal of the patient based on the electrical current. Delivering electrical current to sternal closure wire 205 may generate an impedance that may be sensed. As a basic example, sensor 205 may couple to multiple locations of wire 205 (not shown in FIG. 2) such as areas 216, 217. In doing so, sensor 210 may check impedance across the circuit connecting the multiple locations (i.e., wire 205 extending between portions 216, 217). Sensor 205 may then senses biological signals based on the impedance change. For example, respiration may be sensed due to the changing stresses placed on wire 205 (e.g., between portions 216, 217) as the chest expands based on respiration.

FIG. 5 includes an apparatus 500 in an embodiment of the invention. Apparatus 500 includes a first sensor 520 and a second sensor 525. Both sensors may be coupled to a single wire 530 and/or to different wires 535, 540. In doing so, various perspectives of a signal (e.g., various vectors for ECG) may be determined. One may sense a single biological signal (e.g., heartbeat) using both sensors and then determine a single processed signal (e.g., ECG) based on both sensed signals from the two sensors.

In an embodiment, a single sternal wire may be strung with multiple sensors, which may be of the same type (for a redundancy of sensors of the same parameter) or for sensing different parameters. When a single sternal wire is strung with multiple sensors, the sensors may be placed adjacent other sensors or they may be placed with space and separation between the sensors. By so separating the sensors each sensor may collect its data and signal from a different anatomic location. One example of such placement would be if the sensors were for sensing temperature and two sensors were secured with one each being oriented outwardly towards the skin surface and inwardly toward the heart. The difference in the local temperatures at the sensors and changes over time may be useful to monitor for fever, infection, and to differentiate between these conditions. Another example of such placement would be if the sensors were for sensing electric biopotentials and with one sensor on the right side and another sensor on the left side of the sternal closure. In this example the right sensor's signal could strongly correlate with the V1 vector and the left sensor with the V2 vector (from a 12-lead ECG using skin-surface electrodes).

Since patients may have multiple sternal wires following a single surgery, they may have beads on one or more sternal wires. Individual sensors may sense one or more parameters. This functionality may be programmably controlled before, during, or after implantation. Sensors may sense parameters simultaneously or by intermittently sensing individual parameters. Such intermittent sensing may be referred to as a "duty cycle". In the case of multiple parameters being integrated in the same device, the duty cycle may be the same or different for various parameters or may be programmably controlled before, during, or after implantation.

In an embodiment, conduction velocity, conduction latency, and the like can be measured. For example, electrical current may be supplied to multiple electrodes (with one such electrode being a portion of the sternal wire). Then impedance, conduction velocity, and/or conduction latency related to the current may be used to determine the patient's respiration depth; or cardiac rate, stroke volume and cardiac output. The second (or third or higher number) electrode(s) in such systems may be placed in an appropriate anatomic location to enhance or allow the desired measurements to be made. In an embodiment, any number of vectors to detect respiratory excursion can be used. For example, the absolute rate of excursion and/or vector of excursion can be determined. These parameters may be calculated by changes in wire geometric properties, electric properties (e.g., impedance, conduction velocity of subthreshold currents), and the like.

In an embodiment, one of the multiple electrodes may be external to the patient (and not physically connected to the sternal wire) while the other electrode is part of the sternal wire.

In an embodiment, impedance may be used to assess the build-up of interstitial fluid in the lungs (e.g., a "bio-impedance" of the lungs) by applying a small signal between two points (e.g., one or more sternal wires, beads, external electrodes or electrodes not connected to wire 205, or combinations thereof) that form a line passing through a portion of the lung or lungs. Impedance may be measured between the same two electrodes used to apply the electric signal. Conversely, other electrodes may be used to measure the voltage field created by the applied signal, and the knowledge of this voltage and applied signal may be used to calculate and monitor the relevant impedance.

Figure 3:
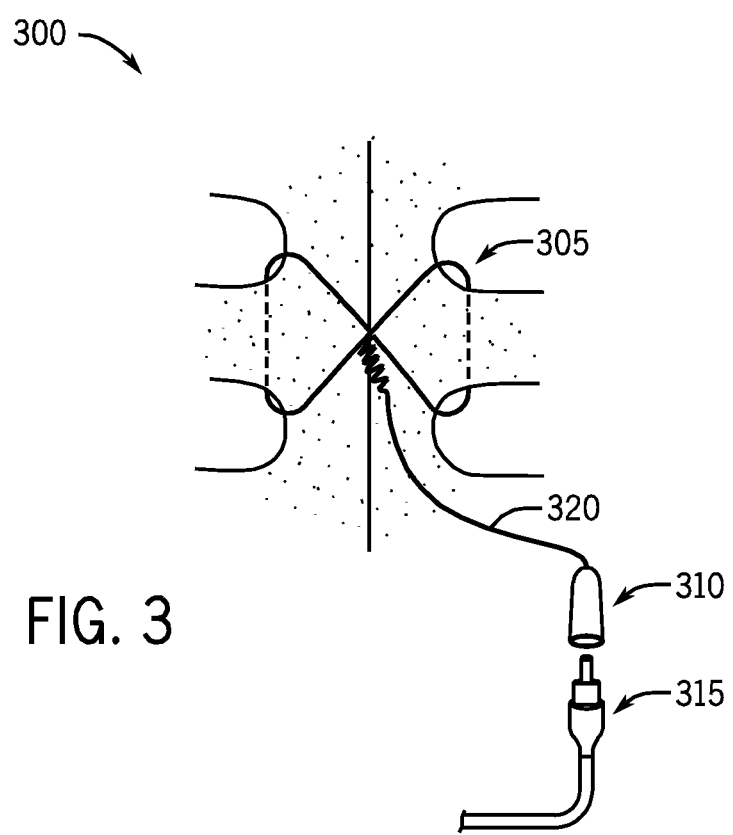
FIG. 3 includes a schematic of a system in an embodiment of the invention.

FIG. 3 includes an embodiment of the invention. Sternal closure wire 305 attaches to a system (e.g., FIG. 7) to acquire one lead (or one vector) of a patient's 12-lead ECG, thus serving as a bioelectrode (electrode). Adaptors/connectors 310, 315 facilitate connection to other instrumentation. Based on the specific anatomic placement of the sternal wire electrode, the vector acquired could strongly correlate with vectors, such as the V1, V2, V3, V4, V5, V6, aVR, aVL, and aVF. Based on the specific anatomic placement, other electrical vectors are also possible such as non-standard vectors (e.g., vertical vectors along sternum such as would be possible in FIG. 5). In an embodiment, any of a series of virtual ECG leads may be created without the need for any external patches, packs, and the like.

Adaptors/connectors 310, 315 and the like may be attached at the time of manufacture for the increased convenience of the surgeon. However, such connectors may be attached at other times. For example, a connector may be inside (or outside) the body after the surgical incision has been closed. In an embodiment a needle affixed to one end of the sternal wire may be passed through the skin nearby the surgical incision (starting from the outside). The user may then continue to manipulate the needle end of the wire while leaving the connector end of the wire on the outside of the body. The connection system at the end of the sternal wire electrode may be designed for "remote" disconnection and removal of a portion of the internal wire in a manner not requiring a surgery for such removal.

In an embodiment, a lead may couple to the sternal wire and extend externally from the patient (e.g., from the patient's chest). External to the patient the lead may couple to an energy source for pacing, defibrillation, cardioversion, sensing, and the like. For example, the system may allow for epicardial pacing using an epicardial pacing wire such as those used for open-chest surgeries. Such a wire may allow for subsequent non-surgical removal from the patient. Various embodiments promote removal of the wire from the patient. For example, to remove the lead wire the lead may couple to the sternal wire at a weakened junction. In an embodiment, the sternal wire/lead junction includes a bond (e.g., weld) that has a lower breaking point than either the sternal wire or the lead itself. Thus, when the lead wire is pulled in tension (by the medical practitioner), the bond breaks before the sternal wire or lead wire. Thus, the lead can be removed without surgery. The lead may be removed 1, 2, 3, 4 or more days after surgery. In an embodiment, the sternal wire/lead junction may have a diminished diameter. Specifically, the sternal wire may have a first diameter, the lead wire may have second diameter, and the sternal wire/lead wire junction may have a third diameter that is smaller than either of the first and second diameters. As such, the third diameter may have a lower breaking point to allow a user to remove the wire by pulling on the wire (with the junction breaking before the sternal wire or lead wire). In other embodiments, other modes for fracturing the sternal wire/lead wire junction may be used. For example, resistive heating via an electric current may be used to cause the junction to fracture. Also, a material used to fuse the junction wire to the lead wire may be selected from a softer material than the lead wire or sternal wire, thus allowing the junction to fail before breaking the sternal or lead wires. In another embodiment, the sternal wire may couple to the lead wire via a crimping coupler joint. For example, the lead wire may fixedly attach to the coupler joint. The coupler joint may be weakly crimped to an end of the sternal wire. Upon pulling the lead wire from the patient the weak crimp joint may fail leaving the sternal wire behind but removing the coupler joint and lead wire.

In an embodiment, the electrode portion and other portions of the sternal wire may be passivated or otherwise treated (e.g., coated) with bio-compatible carbon, relatively non-conductive coatings, and the like to provide surface properties for a bioelectrode (e.g., minimal retention of after-potentials). An end of the wire may be affixed to a needle which enables the wire to be used to sew or suture to biologic material. After the wire is sewn through the tissue and the edges of the incision (or wound) have been approximated, the wire ends may be twisted together or otherwise secured to each other to retain the tissues in a desired orientation. The excess wire protruding from the twist and terminating with the needle may be removed and discarded. However, in an embodiment the excess wire protruding from the twist and terminating with the connector may be preserved, and the connector may be attached to a lead wire 320 (e.g., for sensing a biological signal or applying therapy, as described further below) that connects to medical instrumentation (e.g., amplifier module and/or electrical stimulator) as seen in FIG. 3. The needle attached to the wire may be attached at the time of manufacture for the increased convenience of the user. However, needles may be attached at other times, and with needles being removed and re-attached. This capability of the wires may be desired in some settings to provide for a technique that allows for easy recovery from damaged needles.

In an embodiment a sensor may sense a parameter that is not an electrical bio-potential. For example, a micro electro-mechanical system (MEMS) may be coupled to the coronary artery system to measure local fluid pressure. The MEMS may be coupled to, connected to, or included in the sternal wire's diameter and use a side-window for direct contact of the pressure sensing element with the fluid or blood. Other systems may use sensors to measure general core temperature, local temperature (e.g., thermistor), pH, glucose sensing, oxygen saturation (pO2), and the like (and combinations thereof). With respect to temperature sensing, the sensors may facilitate early detection of infection in or near the sternal incision.

In an embodiment, a sensor may be used for a fully or partially implantable "Holter" recorder for long term ECG monitoring. Some Holter devices are disadvantaged by their lack of electrodes that may be independently located with regard to anatomy to enhance signal strength (e.g., signal noise ratio) or other characteristics and thereby increase the implantable system's ability to provide clinically meaningful data. The inherent electrode placement flexibility associated with an embodiment of the sternal wire invention (e.g., slidably coupling sensor along wire), along with the elimination of some or all electrodes from being disconnected from the skin, help Holter systems acquire quality data. In an embodiment the sternal wire electrode (e.g., 215) may function as one electrode for the Holter monitor while another electrode for the monitor is located elsewhere (e.g., on another sternal wire, another sensor attached elsewhere, a pacemaker or defibrillator chassis or "can", an external patch, a pacemaker or defibrillator lead, a remotely located implantable Holter monitor, unipolar lead, and the like).

In an embodiment, a system includes a power supply to couple to a current source. The current source may deliver electrical current to the patient via a therapeutic shock (e.g., defibrillation or cardioversion). However, the current source may also or alternatively deliver electrical current to the patient via therapeutic pacing (e.g., as with pacemakers).

For example, a sternal wire may be electrically coupled to a device that provides an electrical current/voltage intended to restore a more normal cardiac rhythm. A sensor may couple to a defibrillator/cardioverter to monitor the patient's ECG and determine when a therapeutic energy pulse should be delivered. Post-operative patients who have experienced a thoracotomy or open-chest procedure are at increased risk for atrial fibrillation, ventricular fibrillation, and other cardiac arrhythmias. One or more sternal wires may be used to delivery such therapeutic energy. Also, sternal wires may provide a return path for the energy from defibrillation/cardioversion. When only one sternal wire is so used, another electrode (internal or external) may provide a return path for the electrical charge. Numerous compatible anatomic placement options exist for the electrode(s) needed to provide the return path for the electrical charge (e.g., endovascular electrodes, skin-attached electrodes, esophageal electrode, subcutaneous electrodes, and the like).

Defibrillators range from external and large, to small, hermetically-sealed and completely implantable. External defibrillators may be manual and may require that they be used by trained a medical professional. Alternatively, they may be highly automated for emergent use by non-professionals with no training. Some external defibrillators for patients at high risk of cardiac arrhythmias (including post-operative patients) are "wearable", with the lead system incorporated into a vest. Other highly automatic defibrillators are targeted to the hospitalized CCU patient who is at high risk of cardiac arrhythmias; with the clinical goal of automating and thereby shortening the time from the onset of a fibrillatory cardiac rhythm to the delivery of the defibrillation pulse (as compared to the time required for healthcare workers to respond to a patient's fibrillation and then to deliver a defibrillatory energy discharge).

Defibrillators may utilize a variety of lead systems that help monitor local electrical activity (e.g., ECG) to safely deliver the energy required to restore a more-normal heart rhythm. Based on the specific anatomic placement of the sternal wire electrode (that is coupled to a current source such as an automatic implantable cardiodefibrillator (AICD) or pacemaker), the electrical energy vector of the current may be more or less favorable for achieving the desired clinical results of restoring a more normal cardiac rhythm. Some implantable automatic defibrillator systems may employ subcutaneous electrodes that are surgically implanted, possibly by tunneling the electrodes under the skin (as opposed to making long incisions to permit electrode placement). An embodiment includes a sternal-wire electrode that is used as one or more of the sensing and shocking electrodes of such a subcutaneous defibrillator. Embodiments of the invention may be distinct from these general subcutaneous electrodes for several reasons (e.g., general subcutaneous electrodes do not help in closing a thoracotomy). Other conventional implantable and automatic defibrillator systems may employ only electrodes that are endovascular in design and implanted transvenously. Embodiments of the invention can use sternal wires as one or more than one of the sensing and shocking electrodes of an endovascularly-implantable transvenous defibrillator.

Embodiments of the invention are not necessarily only for sternal applications but may be used in other situations where, for example, wire is used to connect tissues. For example, in some areas of general surgery or orthopedics wire may be used to join tissues (e.g. bones, flesh, organs, vascular tissues, and the like) and the conductive wire and/or associated bead may provide monitoring or therapeutic energy.

An embodiment of sensor 205 may include circuitry such as circuitry depicted in FIG. 4.

Filtering module 705 may receive a sensed biologic signal and filter the signal to remove unwanted noise or frequencies. Amplification module 710 may amplify the received signal for processing and/or telemetry. An analog-to-digital converter 715 may convert analog signals (e.g., sensed biological signal) to a digital signal. The digital signal may be stored in memory 735 or may first be processed by signal processing module 745. Signal processing module 745 may include functions to extract information from the measured signal, or to compress the measured signal to reduce the volume of data to store and transmit. Memory 735 may include both volatile and non-volatile memory, according to various implementations, and may additionally store instructions that can be executed to perform actions. Controller module 720 may provide device control and may include one or more processors that can execute instructions and in response perform actions. Telemetry module 725 may be used, in conjunction with a telemetry antenna, for communication with an external device. Charge reception/control circuitry may optionally be used in implementations that include a rechargeable battery to control reception of charge energy over a charge reception apparatus and coordinate recharging of the battery.

Sensors may contain a battery or other internal source of energy 740 for their functioning. Alternatively sensors beads may utilize a passive design or a transponder design, or sensors may derive the energy for their function from sources within the patient's body. Sensors may also obtain the power they need in a wired manner (e.g., connectors 310, 315).

Data from the sensors may be directed externally (e.g., connector 315) and/or wirelessly (e.g., telemetry block 725 of FIG. 7). Such wireless transmission may employ various wireless data protocols (e.g., Bluetooth) and encryption techniques. For example, a data signal may be transmitted wirelessly to other biomedical equipment used to amplify, filter, process, record, and display the collected information. Short-range digital telemetry protocols may be employed and may provide benefits such as lower transmission energy requirements (to increase battery-life).

Telemetry signals from sensor wires or beads may be collected, stored and/or processed by an appliance that may be worn or carried by the patient, such as in a holster worn attached to their belt, carried in their pocket or purse, or carried/worn in pocket of a special vest. Telemetry signals from sensor wires or beads may be collected, stored and/or processed by an appliance that may be external to the patient but which may be generally nearby to the patient.

Figure 6:
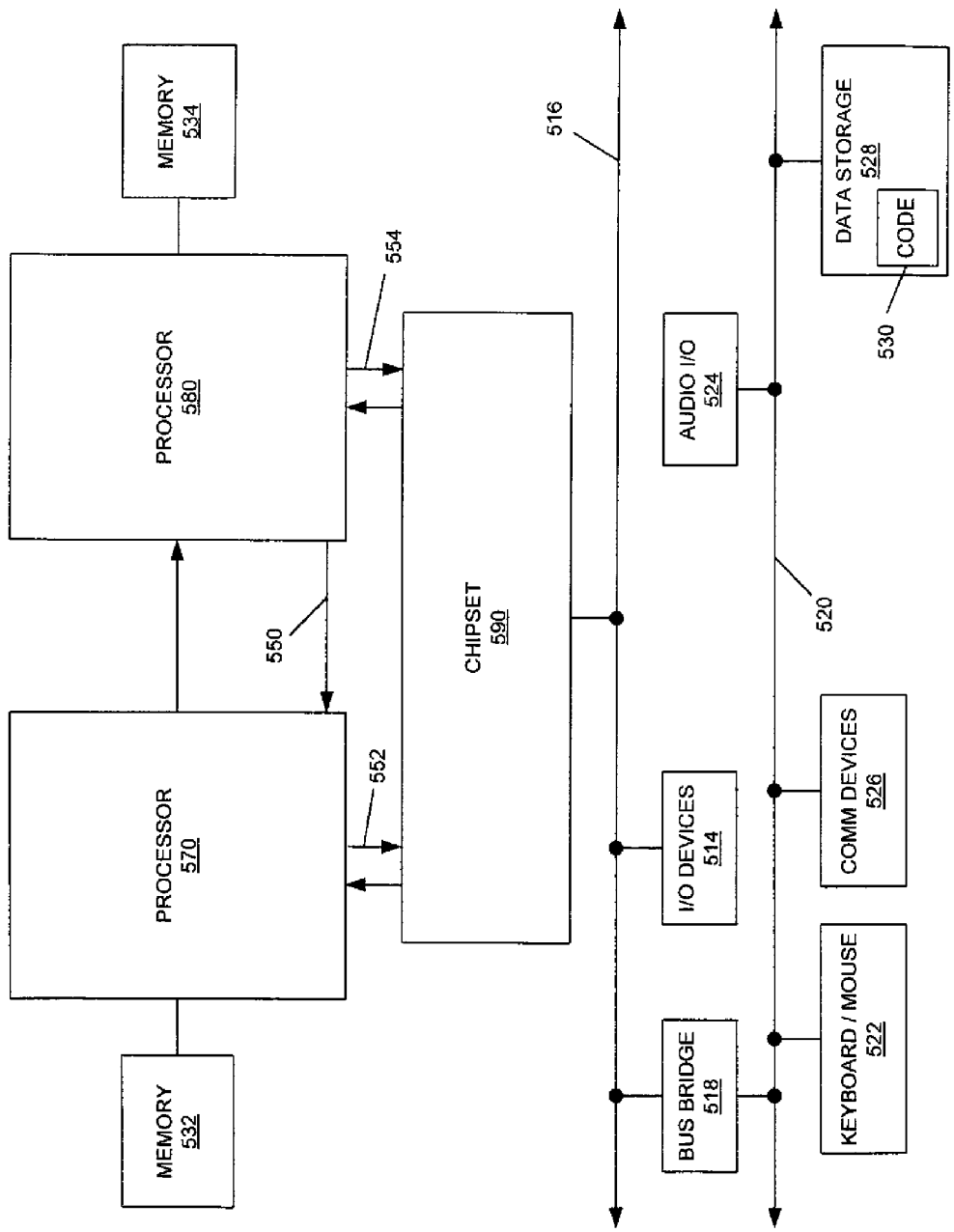
FIG. 6 includes a computer system for use in an embodiment of the invention.

Embodiments may be implemented in many different system types. Referring now to FIG. 6, shown is a block diagram of a system in accordance with an embodiment of the present invention. System 500 may interface a sensor system such as system 700. However, various portions of system 500 may be included in a sensor system itself. Multiprocessor system 500 is a point-to-point interconnect system, and includes a first processor 570 and a second processor 580 coupled via a point-to-point interconnect 550. Each of processors 570 and 580 may be multicore processors. The term "processor" may refer to any device or portion of a device that processes electronic data from registers and/or memory to transform that electronic data into other electronic data that may be stored in registers and/or memory. First processor 570 may include a memory controller hub (MCH) and point-to-point (P-P) interfaces. Similarly, second processor 580 may include a MCH and P-P interfaces. The MCHs may couple the processors to respective memories, namely memory 532 and memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces. Furthermore, chipset 590 may be coupled to a first bus 516 via an interface. Various input/output (I/O) devices 514 may be coupled to first bus 516, along with a bus bridge 518, which couples first bus 516 to a second bus 520. Various devices may be coupled to second bus 520 including, for example, a keyboard/mouse 522, communication devices 526, and data storage unit 528 such as a disk drive or other mass storage device, which may include code 530, in one embodiment. Further, an audio I/O 524 may be coupled to second bus 520.

Embodiments may be implemented in code and may be stored on a storage medium having stored thereon instructions which can be used to program a system to perform the instructions. The storage medium may include, but is not limited to, any type of disk including floppy disks, optical disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions. Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. For purposes of this disclosure, the terms "code" or "program" cover a broad range of components and constructs, including applications, drivers, processes, routines, methods, modules, and subprograms, and may refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered. Components or modules may be combined or separated as desired.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A system comprising:
 a sternal closure wire; and
 a first sensor to slidably couple to the sternal closure wire to provide a user with a plurality of final installation locations for the first sensor along the sternal closure wire;
 wherein in a first mode (a) the sternal closure wire physically couples to the first sensor, (b) the sternal closure wire holds two sternum portions of a patient adjacent to one another, (c) the first sensor senses a first biological signal of the patient, (d) the first sensor processes the first biological signal to generate a processed signal, and (e) the first sensor transmits the processed signal to the user.

2. The system of claim 1, further comprising a current source, wherein in the first mode the current source delivers an electrical current to the sternal closure wire.

3. The system of claim 1, further comprising a current source, wherein in the first mode: the current source delivers an electrical current to the sternal closure wire and generates a corresponding impedance change for the sternal closure wire; and the first sensor senses the first biological signal based on the impedance change.

4. The system of claim 1, wherein the first biological signal is chosen the from the group consisting of ECG, cardiac output, stroke volume, temperature, pH, oxygen saturation, heart rate, and respiration.

5. The system of claim 1, wherein:
the sternal closure wire includes a first portion covered by a first outer insulation covering and a second portion covered by a second insulation covering; and
the first and second insulations coverings are both configured to be selectively removed from the sternal closure wire by the user.

6. The system of claim 1, wherein:
the sternal closure wire is selected from the group consisting of a wire suture and a staple; and
the sensor includes one of a processor and a signal filter.

7. The system of claim 1, further comprising a second sensor to couple to the sternal closure wire;
wherein in the first mode the second sensor senses the first biological signal of the patient, and the processed signal is based on the first and second sensors each sensing the first biological signal of the patient.

8. The system of claim 1, comprising a first electrode that includes the sternal closure wire;
wherein (a) the first biological signal is chosen from the group consisting of ECG and heart rate, and (b) in the first mode the first sensor senses the first biological signal of the patient based on the first electrode.

9. The system of claim 1, comprising a first electrode that includes the sternal closure wire and a second electrode selected from the group comprising an external surface electrode that is external to the patient and an internal electrode that is internal within the patient; wherein the first sensor senses the first biological signal based on the first and second electrodes.

10. The system of claim 1, wherein in the first mode the sternal closure wire directly connects to the first sensor.

11. A system comprising:
a sternal closure wire; and
a first current source to slidably couple to the sternal closure wire to provide a user with a plurality of final installation locations for the first current source along the sternal closure wire;
wherein in a first mode (a) the sternal closure wire holds two sternum portions of a patient adjacent to one another, and (b) the first current source delivers an electrical current to the patient via the sternal closure wire.

12. The system of claim 11, comprising a power supply to couple to the current source, wherein in the first mode the first current source delivers the electrical current to the patient via a therapeutic shock.

13. The system of claim 12, wherein the shock is operable for a therapy selected from the group consisting of defibrillation and cardioversion.

14. The system of claim 11, comprising a power supply to couple to the current source, wherein in the first mode the first current source delivers the electrical current to the patient via therapeutic pacing.

15. The system of claim 11, comprising a lead wire coupled to the sternal wire via a physical junction, the lead wire operable to (a) extend from the sternal wire to outside the patient's chest cavity and to couple to the current source, and (b) disconnect from the sternal wire at the physical junction.

16. The system of claim 11, comprising a first electrode that includes the sternal closure wire and a second electrode selected from the group comprising an external surface electrode that is external to the patient and an internal electrode that is internal within the patient; wherein in the first mode the first current source delivers an electrical current to the patient via the first and second electrodes.

* * * * *